US00PP30121P2

(12) United States Plant Patent
Zaiger et al.

(10) Patent No.: US PP30,121 P2
(45) Date of Patent: Jan. 22, 2019

(54) CHERRY TREE NAMED 'ROYAL FRAN'

(50) Latin Name: *Prunus avium*
Varietal Denomination: Royal Fran

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 15/731,721

(22) Filed: Jul. 24, 2017

(51) Int. Cl.
*A01H 5/08* (2018.01)

(52) U.S. Cl.
USPC ..... Plt./181
CPC ..... *A01H 5/08* (2013.01)

(58) Field of Classification Search
USPC ..... Plt./181
See application file for complete search history.

*Primary Examiner* — Anne Marie Grunberg

(57) ABSTRACT

A new and distinct variety of cherry tree. The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Regular and productive bearer of medium to large size fruit.
3. Fruit with an attractive red skin color.
4. Fruit with good flavor and eating quality with a good balance between acid and sugar.
5. Fruit with firm flesh that has good handling and shipping qualities.

1 Drawing Sheet

Botanical designation: *Prunus avium.*
Variety denomination: 'Royal Fran'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Royal Elaine' Cherry (U.S. Plant Pat. No. 22,603), 'Minnie Royal' Cherry (U.S. Plant Pat. No. 12,942), 'Royal Hazel' Cherry (U.S. Plant Pat. No. 19,920) and the proprietary non-patented cherry seedling selection '24Z399'.

STATEMENT REGARDING FEDERALLY SPONSORED RESEARCH AND DEVELOPMENT

Not applicable.

ORIGIN OF THE VARIETY

The present new variety of cherry tree (*Prunus avium*) was originated by us in our experimental orchard located near Modesto, Calif., as an open pollinated seedling from the proprietary non-patented cherry seedling '24Z399', which originated as a first generation cross between 'Royal Elaine' Cherry (U.S. Plant Pat. No. 22,603) and 'Minnie Royal' Cherry (U.S. Plant Pat. No. 12,942). A large group of these open pollinated seedlings were budded and maintained on established 'Mahaleb' Rootstock (non-patented) to accelerate fruit production for evaluation. Under close and careful observation the present seedling exhibited desirable fruit and tree characteristics and was selected in 2003 for additional asexual reproduction and commercialization.

ASEXUAL REPRODUCTION OF THE VARIETY

In 2003, asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of cherry tree (*Prunus avium*) is of large size, vigorous, upright growth and a regular and productive bearer of large size fruit with an attractive dark red skin color. The fruit is further characterized by having good flavor and eating quality with good handling and shipping qualities. In comparison to its proprietary non-patented cherry seed parent '24Z399' the fruit of the new variety is approximately 10 days earlier in maturity. In comparison to the commercial variety 'Royal Hazel' Cherry (U.S. Plant Pat. No. 19,920) the fruit of the new variety is approximately 5 days later in maturity.

DESCRIPTION OF THE PHOTOGRAPH

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 14 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of a 14 year old specimen grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of approximately 1.5 to 2 meters in height the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive. Produces adequate fruit set annually.

*Bearer*.—Regular, has had adequate fruit set 11 consecutive years. No alternate bearing observed.

*Fertility*.—Self fertile. Sets fruit under the bag.

*Density*.—Medium dense, usually pruned to vase shape to increase amount of sunlight to center of tree to enhance fruit color, Brix and health of fruit spurs.

*Hardiness*.—Hardy in all stone fruit growing areas of California. Tree grown in USDA Hardiness Zone 9. Winter chilling requirement of 500 hours at or below 45° F.

Trunk:

*Size*.—Large, average circumference 71.1 cm at 34.1 cm above ground on a 14 year old tree.

*Stocky*.—Medium stocky.

*Texture*.—Medium shaggy, roughness increases with age.

*Color*.—Varies from 5YR 4/2 to 5YR 2/2.

Branches:

*Size*.—Medium. Average circumference 25.4 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 10 in a 25.8 square cm area. Average length 7.7 mm. Average width 2.5 mm. Color varies from 10YR 6/8 to 10YR 5/8.

*Color*.—New growth varies from 5GY 6/8 to 5GY 6/10. Mature growth varies from 10YR 4/2 to 10YR 3/2, varies with age of growth.

Leaves:

*Size*.—Large. Average length 159.2 mm. Average width 72.1 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 52.1 mm. Average width 2.1 mm. Longitudinally grooved. Surface — glabrous. Color varies from 5GY 7/8 to 5GY 6/8.

*Glands*.—Type — reniform. Size — large. Average length 2.4 mm. Average diameter 1.6 mm. Average number 2, varies from 1 to 2. Located primarily on upper portion of petiole and base of the leaf blade. Color varies from 5GY 5/8 to 5YR 3/6.

*Stipules*.—Average number 2. Average length 11.4 mm. Edges — pectinate. Color varies from 5GY 8/6 to 2.5YR 3/6.

*Color*.—Upper surface varies from 7.5GY 3/6 to 7.5GY 2/4. Lower surface varies from 7.5GY 5/4 to 7.5GY 4/4. Midvein varies from 5GY 7/8 to 5GY 6/8.

Flower buds:

*Size*.—Large. Average length 16.1 mm. Average diameter 9.2 mm.

*Hardiness*.—Hardy with respect to California winters.

*Density*.—Very dense.

*Form*.—Conical, becoming elongated just before opening.

*Pedicel*.—Average length 10.8 mm. Average width 1.3 mm. Surface — glabrous. Color varies from 2.5GY 5/8 to 5GY 5/8.

*Color*.—Varies from N 9.5/(white) to 2.5R 4/8 on upper edge of petals.

*Number of buds per spur*.—Average number 3, varies from 2 to 5.

Flowers:

*Blooming period*.—Date of First Bloom Feb. 22, 2017. Date of Petal Fall Mar. 2, 2017, varies slightly with climatic conditions.

*Size*.—Large. Average height 20.5 mm. Average diameter 37.0 mm.

*Petals*.—Number — normally 5, alternately arranged to sepals. Size — large. Average length 19.2 mm. Average width 16.4 mm. Form — elliptical. Arrangement — free to slightly overlapping. Petal apex — rounded. Petal base — rounded to somewhat truncate. Margin — sinuate. Color N 9.5/(white). Both upper and lower surfaces glabrous.

*Sepals*.—Number — normally 5, alternately arranged to petals. Size — large. Average length 8.6 mm. Average width 6.4 mm. Shape — triangular. Apex — rounded to triangular. Margin — entire. Both upper and lower surfaces glabrous. Color — upper surface varies from 2.5GY 5/8 to 5GY 5/8. Lower surface varies from 5GY 5/8 to 5R 3/6.

*Stamens*.—Average number per flower 35. Average filament length 13.0 mm. On average the stamens, are below the height of the petals. Filament color N 9.5/(white). Anther color varies from 5Y 8/8 to 5Y 8/10.

*Pollen*.—Self fertile, sets fruit under the bag. Color varies from 2.5Y 7/12 to 5Y 7/12.

*Pistil*.—Normally 1. Average length 14.9 mm. Position of stigma an average of 3.6 mm below anthers. Surface — glabrous. Color varies from 10Y 7/6 to 2.5GY 7/8.

*Fragrance*.—Slight.

*Color*.—N 9.5/(white).

*Pedicel*.—Large. Average length 18.5 mm. Average width 1.3 mm. Color varies from 5GY 6/8 to 5GY 5/8.

*Number flowers per flower bud*.—Average 3, varies from 2 to 3.

Fruit:

*Maturity when described*.—Firm ripe and ready for consumption.

*Date of first picking*.—May 14, 2017.

*Date of last picking*.—May 24, 2017, varies slightly with climatic conditions.

*Size*.—Medium to large. Average diameter axially 26.5 mm. Average transversely in suture plane 23.2 mm. Average across suture plane 29.4 mm. Average weight 11.5 grams, varies with fertility of the soil, amount of thinning and climatic conditions.

*Form*.—Globose to slightly oblong.

*Suture*.—Nearly smooth.

*Ventral surface*.—Slightly lipped.

*Apex*.—Nearly rounded to slightly retuse.

*Base*.—Retuse.

*Stem cavity*.—Rounded. Average depth 2.1 mm. Average breadth 3.7 mm.

Stem:

*Size*.—Medium to large. Average length 34.6 mm. Average diameter 1.9 mm.

*Color*.—Varies from 5GY 6/6 to 5GY 6/8.

Flesh:

*Ripens*.—Evenly.

*Texture*.—Firm.

*Fibers*.—Few, small, tender.

*Firmness*.—Firm, comparable to other commercial cherry varieties.

*Aroma*.—Slight.

*Amydgalin*.—Undetected.

*Eating quality*.—Good.

*Flavor*.—Good, with a good balance between acid and sugar.

*Juice*.—Heavy amount, enhances flavor.

*Acidity*.—Not available.

*Brix*.—Average Brix 17.5°, varies slightly with amount of fruit per tree and climatic conditions.

*Color*.—Varies from 5R 3/8 to 5R 3/10.

*Pit cavity*.—Average length 12.4 mm. Average width 10.4 mm. Average depth 4.0 mm. Color varies from 7.5R 2/6 to 7.5R 2/8.

Skin:

*Thickness*.—Medium.

*Surface*.—Smooth.

*Bloom*.—Wanting.

*Tendency to crack*.—None during dry weather, only slight tendency to crack in wet weather. Depends on stage of maturity.

*Color*.—Varies from 7.5R 3/12 to 7.5R 3/10.

Stone:

*Type*.—Clingstone, weak adherence to flesh.

*Size*.—Medium. Average length 11.9 mm. Average width 9.8 mm. Average thickness 7.1 mm.

*Form*.—Ovoid.

*Base*.—Flat.

*Apex*.—Round.

*Surface*.—Very slightly pitted throughout. Small ridges run along each side of the suture line from base to apex.

*Sides*.—Varies from equal to unequal with one side extending further from the suture plane.

*Ridges*.—Relatively smooth. A small, narrow ridge on each side of suture extending from base toward apex.

*Tendency to split*.—None.

*Color*.—Varies from 5YR 6/6 to 5YR 5/6 when dry.

Kernel:

*Size*.—Small to medium. Average length 8.4 mm. Average width 5.6 mm. Average depth 4.5 mm.

*Form*.—Ovoid.

*Viability*.—Viable, complete embryo development.

*Skin color*.—10Y 9/2.

Use:

*Dessert*.—Market — local and long distance.

Keeping quality: Good, held firm in cold storage for 2 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of cherry tree, its flowers foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of cherry tree (*Prunus avium*), substantially as illustrated and described.

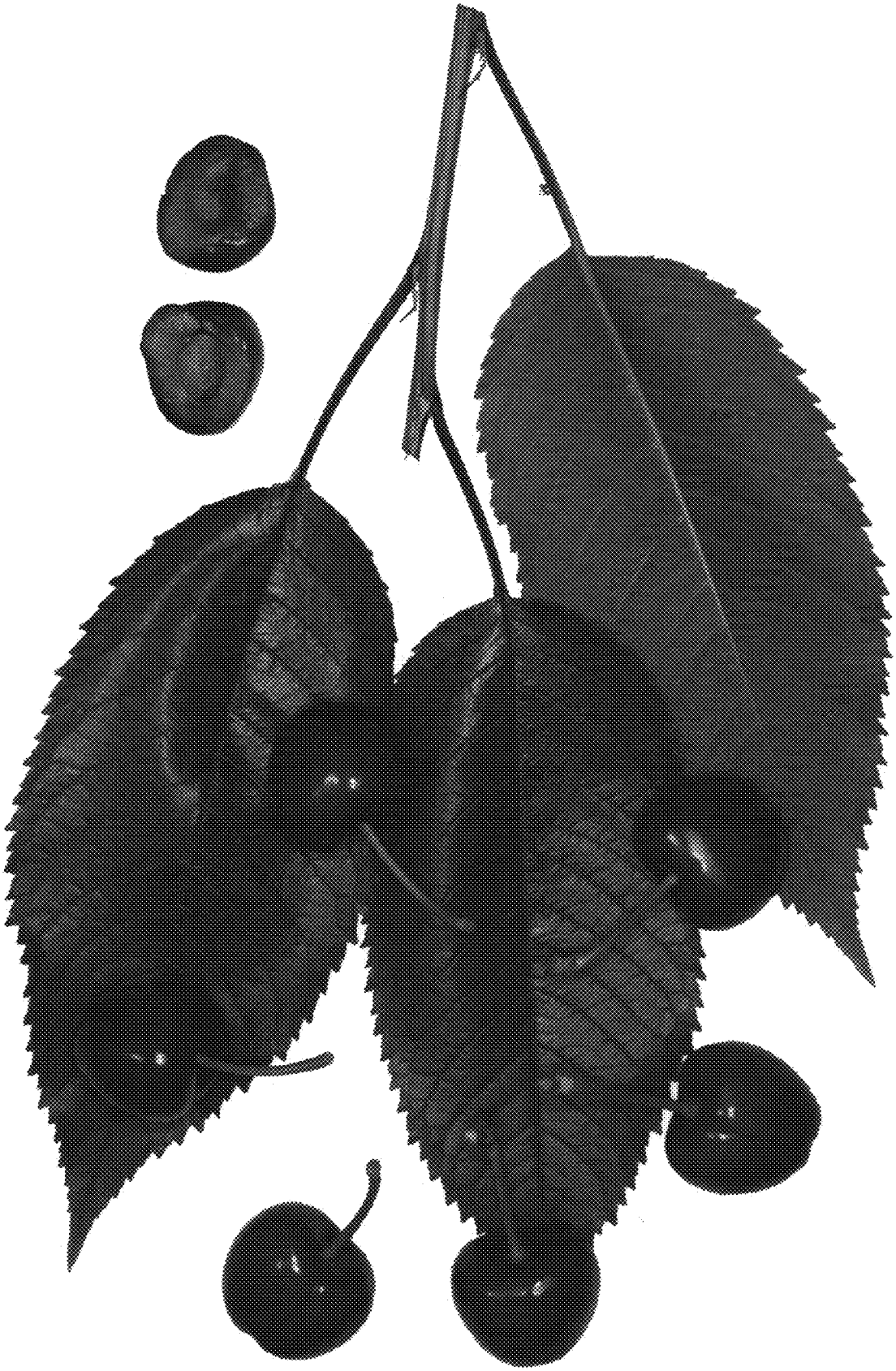

* * * * *